(12) United States Patent
Barron

(10) Patent No.: US 8,636,985 B2
(45) Date of Patent: Jan. 28, 2014

(54) FUNCTIONAL FORMULATION IN CHEWING GUM

(76) Inventor: Jon Barron, Chatsworth, CA (US)

( * ) Notice: Subject to any disclaimer, the term of this patent is extended or adjusted under 35 U.S.C. 154(b) by 0 days.

(21) Appl. No.: 13/296,034

(22) Filed: Nov. 14, 2011

(65) Prior Publication Data

US 2012/0121520 A1    May 17, 2012

Related U.S. Application Data

(60) Provisional application No. 61/381,910, filed on Nov. 16, 2010.

(51) Int. Cl.
*A61K 36/81* (2006.01)
*A61K 9/68* (2006.01)
*A61P 25/00* (2006.01)

(52) U.S. Cl.
USPC ............................................. 424/48; 424/725

(58) Field of Classification Search
None
See application file for complete search history.

(56) References Cited

U.S. PATENT DOCUMENTS 7,476,406 B1 *    1/2009   Smidt ........................... 424/729
2006/0018975 A1 *   1/2006   Talbott .......................... 424/646

OTHER PUBLICATIONS

Hao Zhang, Jie Zhang and James B. Streisand. Oral Mucosal Drug Delivery: Clinical Pharmacokinetics and Therapeutic Applications. Clin Pharmacokinet 2002; 41 (9): 661-680.*
Archana, R., et al., Antistressor effect of *Withania somnifera*, Journal of Ethnopharmacology (1999) 64:91-93.
Bhattacharya, S.K., et al., Antistress Acitivity of Sitoindosides VII and VIII, New Acylsterylglucosides from *Withania somnifera*, Phytotherapy Res. (1987) 1:32-37.
Bhattacharya, S.K., et al., Effects of Glycowithanolides from *Withania somnifera* on an Animal Model of Alzheimer's Disease and Perturbed Central Cholinergic Markers of Cognition in Rats, Phytotherapy Res. (1995) 9:110-113.
Bryan, J., Psychological effects of dietary components of tea: caffeine and L-theanine, Nutrition Reviews (2008) vol. 66(2):82-90.
Dhuley, J.N., Effect of ashwagandha on lipid peroxidation in stress-induced animals, Journal of Ethnopharmacology (1998) 60:173-178.
Haskell, C.F., et al., The effects of L-theanine, caffeine and their combination on cognition and mood, Biological Psychology (2008) 77:113-122.
Kimura, K., et al., L-Theanine reduces psychological and physiological stress responses, Biological Psychology (2007) 74:39-45.
Mason, R., L-Theanine Boosts Alpha Waves, Promotes Alert Relaxation, Alternative & Complementary Therapies (Apr. 2001) 91-96.
Mishra, L-C., et al., Scientific Basis for the Therapeutic Use of *Withania somnifera* (Ashwagandha): A Review, Alternative Medicine Rev. (2000) 5(4):334-346.
Nobre, A.C., et al., L-theanine, a natural constituent in tea, and its effect on mental state, Asia Pac. J. Clin. Nutr. (2008) 17:167-168.
Rogers, P.J., et al., Time for tea: mood, blood pressure and cognitive performance effects of caffeine and theanine administered alone and together, Psychopharmacology (2008) 195:569-577.
Vaidya, A.D.B., The status and scope of Indian medicinal plants acting on central nervous system, Indian Journal of Pharmacology (1997) 29:S340-S343.

* cited by examiner

*Primary Examiner* — Brian Gulledge
*Assistant Examiner* — Michael P Cohen
(74) *Attorney, Agent, or Firm* — Amin Talati, LLC; George M. Carrera, Jr.

(57) ABSTRACT

Nutraceutical gum or functional food compositions comprise Ashwagandha (*Withania somnifera*) and L-theanine in a sublingual formulation. Methods of making suitable sublingual formulations are described. Also provided is a method for reduction of stress and/or enhancement of energy and mental clarity, comprising administering to an individual in need thereof an effective amount of a nutritional composition comprising Ashwagandha herb and L-theanine, and a nutraceutically acceptable carrier, wherein the nutritional composition is administered sublingually.

4 Claims, No Drawings

FUNCTIONAL FORMULATION IN CHEWING GUM

This application claims the benefit of earlier filed U.S. Provisional Application No. 61/381,910, filed on Nov. 16, 2010, which is hereby incorporated by reference herein.

FIELD OF THE INVENTION

A nutraceutical gum or functional food composition comprises Ashwagandha (*Withania somnifera*) and L-theanine Embodiments of the formulation include ingredients balanced in a synergistic manner to elicit complementary effects which provide reduction of stress and alleviation of fatigue, enhancement of energy and a boost in mental clarity and concentration. Methods of making suitable sublingual formulations are described.

BACKGROUND

In countries where traditional medicine is practiced, particularly in the East, it has been estimated that up to 80% of the population continues to use these traditional methods to treat primary medical problems. In the past decade or so, research has been increasingly focused on scientific evaluation of traditional medicines and drugs of plant and herbal origin, including methods derived from indigenous or tribal populations.

One such herb is Ashwagandha (*Withania somnifera*), so named in Sanskrit denoting its rejuvenative or vital properties (ashwa: horse; gandha: smell), which is said to confer the strength and vitality of a horse. This herb has long been used in the Ayurvedic formulary of India. Ashwagandha is commonly referred to as "Indian Ginseng" because of its beneficial properties. See, M. S. Premila, *Ayurvedic Herbs: A Clinical Guide to the Healing Plants of Traditional Indian Medicine* (2007, The Haworth Press, New York).

Herbalists have identified Ashwagandha as an adaptogen. The term "adaptogen" is used herein to refer to natural herb products which are believed to increase the body's resistance to stress, trauma, anxiety and fatigue. In the past, adaptogens have been called rejuvenating herbs, restoratives, qi (i.e. "chi") tonics, or rasayanas. While not intending to be bound by theory, it has been proposed that adaptogenic herbs have a "normalizing effect" on the body and may be capable of either toning down the activity of hyperfunctioning body systems, or strengthening the activity of hypofunctioning body systems. For example, it has been proposed that adaptogenic herbs have the ability to balance endocrine system hormones and the immune system, and thus help the body to maintain homeostasis.

Other well known herbal adaptogens include licorice, ginseng, Reishi, and Astragalus. These useful herbs have been often studied in recent years as components in nutraceuticals, dietary supplements, and as dietary ingredients in functional foods.

Another compound associated with relaxation and reduction of stress is L-theanine (N-ethyl-L-glutamine), which is a component found in both green and black tea. Tea is the only significant dietary source of L-theanine, and it has been proposed that L-theanine can induce a relaxed state. As an amino acid derivative, L-theanine rapidly crosses the blood-brain-barrier and thereby acts directly on the brain. L-theanine has been studied in combination with caffeine, which reveals synergistic effects in cognition and mood (C. F. Haskell, et al., *Biol. Psychol.* (2008) 77: 113-122).

The adaptogenic properties of Ashwagandha herb would appear to complement the anti-stress property of L-theanine. If Ashwagandha herb and L-theanine were combined, the resulting nutraceutical would provide a useful contribution to the art.

In view of the above, there is a need and a desire for a dietary supplement and/or functional food including Ashwagandha herb and L-theanine in combination, that exploits the potential beneficial properties of both components in a readily bioavailable formulation.

SUMMARY OF THE INVENTION

In one embodiment, the invention relates to a nutritional gum composition comprising Ashwangandha herb and L-theanine in combination with a nutraceutically acceptable carrier.

In another embodiment, a method for making a nutritional gum composition comprising Ashwangandha herb and L-theanine is provided.

Also provided is a method for reduction of stress and/or enhancement of energy and mental clarity, comprising administering to an individual in need thereof an effective amount of a nutritional composition comprising Ashwagandha herb and L-theanine, and a nutraceutically acceptable carrier, wherein the nutritional composition is administered sublingually.

DETAILED DESCRIPTION

A nutritional composition comprising a complementary combination of Ashwagandha herb and L-theanine has been discovered. Use of the two components singularly does not produce the desired effects of stress reduction and enhancement of energy and/or mental clarity, nor does oral delivery through traditional pill form, nor by ingestion or in a beverage, of the two components either singularly or in combination as part of functional foods absorbed in the intestine. The advantageous effects are achieved only by combining the two ingredients in a rapidly absorbed sublingual or buccal formulation, or through some other equivalent delivery system that is rapidly absorbed by the oral or nasal mucosa. One useful sublingual, functional food delivery system includes chewing gums or confectionaries. Other sublingual delivery systems include, but are not limited to, dissolvable tabs placed under and/or on the tongue, liquid drops, beverages, oral dissolvable films or oral dissolvable strip technology. These techniques include edible films and effervescent-edible substances.

Sublingual use of the combination of Ashwagandha herb and L-theanine provides rapid delivery of the active ingredients to the bloodstream and rapid onset of beneficial effects to the user, including relaxation, stress reduction, and satiety, among others. The ease of use and speed of onset through sublingual delivery provides value to the user and an unexpected synergistic effect. As defined herein, the term "stress" is generally defined as an absence or lack of relaxation, or the presence of anxiety, and/or the loss of a general sense of well-being in an individual or human patient.

Because Ashwagandha herb and L-theanine produce different but complementary effects on the human body and its systems, varying the ratio of the two ingredients has been found to advantageously change the effects experienced by human subjects. Amounts of the two ingredients Ashwagandha herb and L-theanine in the embodiments of the invention will vary according to the effect desired.

Ashwagandha herb can be provided, for example, in Ashwagandha root extract powder, standardized to greater than 5% withanolides by weight. Ashwagandha root extract can be obtained containing negligible amounts of withaferin A (less than 0.1%), however, in other embodiments withaferin A can be contained in Ashwagandha herb or added to the formulation. Suitable Ashwagandha extract is available, for example, from Nutragenesis (Brattleboro, Vt.). Useful ranges of Ashwagandha herb can be from about 10 mg to about 250 mg, or preferably from about 70 mg to about 150 mg, in combination with an effective amount of L-theanine. One suitable range of Ashwagandha herb is from about 70 mg to about 110 mg, in combination with an effective amount of L-theanine. The ranges of bioactive components are generally expressed per serving. A useful dose can include one or more servings.

Useful ranges for L-theanine (for example, available from Purebulk, Pharhome International Limited, Guangdong, China) can be from about 20 mg to about 200 mg, or preferably from about 50 mg to about 125 mg, in combination with an effective amount of Ashwagandha herb. One suitable range of L-theanine is from about 80 mg to about 120 mg, in combination with an effective amount of Ashwagandha herb. The ranges of bioactive components are generally expressed per serving. A useful dose can include one or more servings. For example, a useful dose is about 200 mg of L-theanine and about 160 mg of Ashwagandha, which can be provided in one or more servings, for example, in a gum piece. In another example, two servings of a single gum piece including about 100 mg of L-theanine and about 80 mg of Ashwagandha would provide the aforementioned dose. In one embodiment, a finished gum piece containing useful and effective amounts of both L-theanine and Ashwagandha can range in weight from about 1700 mg to about 2300 mg. In another embodiment, the finished gum piece containing useful and effective amounts of both L-theanine and Ashwagandha is about 2000 mg.

L-Theanine can be obtained at purity levels of 95%, or higher, which is useful in embodiments of the present invention. L-Theanine may take the form of a salt, alternatively an internal salt, or an addition salt of an appropriate acid or base. Suitable acid addition salts may be prepared from an inorganic acid or from an organic acid. Examples of inorganic acids include hydrochloric, hydrobromic, sulfuric, phosphoric, and the like, or combinations thereof. Examples of organic acids include acetic, succinic, gluconic, lactic, malic, tartaric, citric, ascorbic, maleic, fumaric, pyruvic, aspartic, glutamic, benzoic, trifluoroacetic, stearic, and the like, or combinations thereof. Suitable base additions salts include, for example, metallic salts including alkali metal, alkaline earth metal and/or transition metal salts, such as, for example, calcium, magnesium, potassium, sodium, lithium, and zinc salts. Pharmaceutically acceptable base addition salts also include organic salts made from basic amines, such as, for example, N,N'-dibenzylethylenediamine, chloroprocaine, choline, diethanolamine, ethylenediamine, meglumine (N-methylglucamine), tromethamine (tris(hydroxymethyl) aminomethane), and procaine.

Because Ashwagandha and L-theanine produce different but complementary effects in the human body, varying the ratio of the two ingredients changes the effect experienced by the body. With that in mind, amounts for the two ingredients in any particular embodiment of the invention will vary according to the effect desired. Taking into consideration the component ranges described above, when greater relaxation is desired, the ratio of Ashwagandha to L-theanine will be higher. When greater reduction of stress or mental clarity is required, the ratio of L-theanine to Ashwagandha will be higher.

In an embodiment, an effective sublingual formulation comprises a gum, a confection, or a dissolvable tab/tablet. One formulation comprises a chewing gum having Ashwagandha extract in an amount from about 70 mg to about 110 mg, in combination with L-theanine in an amount from about 80 mg to about 120 mg, and a nutraceutical carrier. Optionally, the chewing gum can include bergamot, chamomile, and/or lavender extracts. Optionally sweeteners can be added including, but not limited to xylitol (Chemaster International Inc., Qingdao, China), sorbitol (Pure Chem, Ltd., Bangkok, Thailand), isomalt (Chemaster International Inc., Qingdao, China), maltitol (Pure Chem, Ltd., Bangkok, Thailand), Stevia or Stevia extract (90% by weight available from Shaanxi Run-time Bio-technology Development Co., Ltd, Shaanxi, China), and the like, or combinations thereof. Useful excipients and fillers in said formulations include gumbase, gum arabic, magnesium stearate (Hangzhou Ruijiang Chemical Co., Ltd., Zhejiang, China), calcium stearate, carnauba wax (ChemCor, Chester, N.Y.), titanium dioxide (Shanghai Weiyi Industrial Co., Ltd., Shanghai, China), silicon dioxide (Hangzhou Ruijiang Chemical Co., Ltd., Zhejiang, China), modified food starch (Angel Starch & Chemicals Pvt Ltd, Tamil Nadu, India), and the like, or combinations thereof. Useful powdered gumbases include CPG from Gum Base Co. (Milan, Italy). Another suitable gumbase is available from Gumlink (Vejle, Denmark). Natural flavors and/or flavorants can include, but are not limited to, natural vanilla, sweet peppermint, menthol, menthol powder, and the like, or combinations thereof. Artificial flavors can be used. Suitable natural and artificial flavors are available from Flower Flavours & Fragrances Co., Ltd., (Guangdong, China). Natural colors can include, but are not limited to, titanium dioxide white. Coatings, for example, pharmaceutical glaze or confectioner's glaze (Austrade Incorporated, Palm Beach Gardens, Fla.), can be used.

The gum embodiment can be designed to maximize sensations of relaxation and satiety, among other effects. For example, other primary effects of Ashwagandha (*Withania somnifera*) and L-theanine can include: (1) reduction of stress, i.e. general relaxation: specifically by helping to increase resistance to fatigue, stress, and tension, by assisting the body to cope with stress, and by promoting a feeling of well-being; (2) energy: specifically by enhancing energy levels while helping to alleviate or reduce fatigue, by restoring and sustaining energy levels, building and/or boosting energy, and building physical stamina; (3) mental cognition: specifically by helping to alleviate mental fatigue, helping to sharpen focus and mental stamina, and boosting mental clarity and concentration; (4) weight management: specifically by helping to control stress-related eating, inhibiting and controlling stress-related overeating, and managing stress-induced appetite; (5) glucose release, specifically by helping to balance blood sugar levels; (6) immune support: specifically by promoting healthy immune function, by supporting cellular defenses, e.g., immunomodulation, by supporting the body's immune defenses, and by enhancing macrophage production; (7) adaptogenic: specifically by helping to regulate and balance healthy metabolic function, enhancing energy levels while helping to alleviate fatigue (as discussed above), by providing adapation to stress, and normalizing effects; and (8) anti-aging: specifically by helping to slow the effects of aging by inhibiting oxidative damage to cells and tissues, by attenuating the effects of pro-oxidative cellular damage, and by protecting against free radical damage to cells.

Components in the Gum Formulation

Ashwagandha (*Withania somnifera*) is an erect shrub found growing wild throughout the hotter parts of India and is cultivated for its roots, which are well known in Ayurveda for their rejuvenative or rasayana properties. The roots contain 0.2-0.3% of alkaloids and withaferin A together with several withanolides, which are C-28 steroidal lactones of the ergostane type. In addition, the roots contain starch, reducing sugars, hentriacontane ($C_{31}$-normal alkane), and a number of amino acids. Also present are sitoindosides VII and VIII, which are acylsteryl glucosides, and sitoindosides IX and X, which are C-28 glycowithanolides that may contribute to the adaptogenic properties found in this herb. There are several chemotypes of the plant Ashwagandha (*Withania somnifera*) available with varying amounts of the various sitoindosides. See, M. S. Premila (2007), *Ayurvedic Herbs*, and references cited therein.

Ashwagandha (*Withania somnifera*) root powder, root methanol extract, and its active principles (a mixture containing equimolar concentrations of withaferin A and sitoindosides VII-X), have been shown to possess antioxidant activity, which may explain the antistress, anti-inflammatory, immunomodulatory, and cognition-enhancing and rejuvenative effects shown in experimental and clinical studies. Withaferin A has been shown to have anti-inflammatory and antiarthritic properties in several experimental models. See, M. S. Premila (2007), *Ayurvedic Herbs*, and references cited therein.

With respect to CNS activity, defined extracts of Ashwagandha (*Withania somnifera*) consisting of mixtures of sitoindosides VII-X and withaferin A prepared by combination of equimolar amounts of the compounds taken from *Withania somnifera* induced an increase in the cortical muscarinic acetylcholine capacity, which may partly explain the cognition-enhancing effects seen both in animals and humans (*Neurochem. Int.* (1997) 30:181-190).

In human clinical trials for arthritis, use of up to 6 g of Ashwagandha (*Withania somnifera*) root powder for 3-4 weeks was well tolerated (*Indian J. Med. Res.* (1968) 56:1581-1583). In a long-term trial on healthy volunteers in the age group of 50-59 years to study its tonic antiaging effect, 3 g of the root powder in three divided doses for one year showed no untoward side effects (*J. Res. Ayur Siddha* (1980) 1:247-258).

In animal models, acute toxicity and a 4-week subacute study with aqueous extract of Ashwagandha (*Withania somnifera*) in doses from 50 mg/kg to 1 g/kg showed no toxic effects, and no hepatic or renal toxicity (*Phytother. Res.* (1999) 13:275-291). Also, chronic feeding of Ashwagandha at 100 mg/kg for 180 days did not show any toxicity or significant changes in the biochemical profile of blood (*J. Ethnopharmacology* (2000) 70:57-63).

L-Theanine has been found primarily in green and black tea species. L-Theanine (N-ethyl-L-glutamine) is an amino acid derivative found in species of *Camellia* and in the edible bay boletes mushroom *Xerocomus badius*, but is otherwise rare in nature. It is the major amino acid in tea and is thought to be a flavorous constituent of tea leaves. L-Theanine constitutes between 1% and 2% of the dry weight of tea which corresponds to about 25 mg to about 60 mg per 200 mL serving.

L-Theanine readily crosses the blood-brain barrier in a dose-dependent manner to exert its effects directly on the brain within about 30 minutes. L-Theanine can reach maximal levels 5 hours after ingestion in animals, and it is thought to influence the central nervous system (CNS) through a variety of mechanisms, including effects on neurotransmitters (J. Bryan, *Nutrition Reviews* (2007) 66:82-90). L-Theanine significantly modulates the resting state of brain activity. After administration of L-theanine, increases in alpha band activity supports a role for this agent in achieving a relaxed, but alert mental state via a direct influence on the CNS (Nobre, et al., *Asia Pac. J. Clin Nutr.* (2008) 17:167-168). Furthermore, L-theanine can induce a mild, relaxing effect when consumed in foods and beverages.

After ingesting Ashwagandha and L-theanine as supplements or part of functional foods, it requires that the extracts spend an hour or longer in the stomach before passing into the small intestine where absorption begins—at which point, it will take an additional 2-3 hours for the herbs to fully cross the intestinal wall and make their way into the bloodstream. The herbs will have an effect, but the effect is spread out over so much time that the effect will not be readily noticed under normal circumstances by the user.

On the other hand, by providing a sublingual delivery system that keeps the extracts in maximum contact with the blood vessel rich tissues of the mouth for the longest possible time, large amounts of the active components make their way directly into the bloodstream through the mouth in a matter of 30-120 seconds and from there go directly into the brain. Consequently, the desired effects (relaxation, satiety, smooth energy, mental clarity, etc.) are experienced strongly and almost immediately.

Also contemplated in certain embodiments is the addition of other suitable and advantageous and/or complementary herbs, herbal extracts, and nutraceuticals. The addition of other herbal extracts and nutraceuticals can help to push the effects further in any desired direction. For example, the addition of herbs such as bergamot, lavender, and/or chamomile to the invention will push a given formulation embodiment more towards relaxation. The addition of bacopa and/or green tea (including caffeine) will produce a non jittery energy in the formulation embodiment. The addition of gingko biloba will increase blood flow to the brain and augment the mental clarity aspects of the formulation embodiment.

Additional Components

Gotu Kola Leaf has been referred to as "food for the brain." This Ayurvedic herb has demonstrated the ability to improve mental functions such as concentration and memory. It has a calming effect on the body and is chiefly used to support the central nervous system. In effect, regular use of Gotu kola can rebuild mental energy reserves. Gotu kola can be helpful in dealing with attention deficit disorder (ADD), since it increases the ability to focus while having an overall soothing and relaxing effect on the nervous system.

Calamus Root is traditionally used for its ability to "stimulate" the mind and evoke a cheerful mood. Years ago, Canadian trappers regularly chewed it as a stimulant whenever tired—a trick they learned from the Cree Indians, who used calamus to fight the effects of exhaustion or fatigue, and to help treat or prevent hangovers.

Rosemary Leaf is a valuable circulatory stimulant, with a particular affinity for cerebral circulation. It is a stimulating tonic herb useful for those suffering from depression or nervous exhaustion—and is extremely helpful in improving memory and concentration. In fact, that is why Rosemary is traditionally let at gravesides and handed to the bereaved—for remembrance.

Kola Nut contains 1.5-2% caffeine, plus theobromine (an alkaloid similar to caffeine) that increases cerebral circulation. Kola is believed to promote better concentration and a "clearing" of the head. When limited amounts of Kola nut are consumed in a formulation, and because its actives go straight to the brain, its stimulatory effect is limited to the brain and has very little impact on the adrenals, unlike coffee.

Cayenne is used as a catalyst in many herbal formulas. It may help to drive the other herbs into the bloodstream. In an embodiment, when used in a tincture that is taken sublingually, it can help to accelerate transport of active components of the other herbs directly into the brain, which is one of the reasons this formula is so effective.

Periwinkle is used as a cerebral vasodilator for enhancing mental alertness. It increases blood flow to the brain and improves its oxygenation. Vinpocetine, from the extract of the periwinkle plant, has over 100 clinical trials proving that periwinkle improves cerebral metabolism, increases cerebral blood flow, increases use of glucose and oxygen in the brain, increases serotonin levels, etc.

Any of the additional components can optionally be used in a nutritional formulation having a combination of Ashwagandha herb and L-theanine. The nutritional formulations described herein can be included in nutraceutical products and functional foods. Preferred nutritional formulations described herein comprise sublingual and buccal preparations.

Delivery System

The use of sublingual delivery in the invention makes a vital difference in the end product. Normal ingestion of functional foods takes several hours for complete release of the bioactive components, as they must make their way from the stomach into the small intestine, where absorption takes place—again over several hours. This means the impact of the actives is spread out over several hours.

Sublingual use of the combination of Ashwagandha herb and L-theanine provides rapid delivery of the active ingredients to the bloodstream and rapid onset of beneficial effects to the user, including relaxation, stress reduction, and enhancement of energy with mental clarity, among others. The ease of use and speed of onset through sublingual delivery provides value to the user and an unexpected synergistic effect. Suitable methods of administration include, but are not limited to, sublingual, buccal, oral, intranasal, inhalational, and the like.

Suitable dosage forms include tablets, capsules, solutions, suspensions, powders, gums, and confectionaries. Other sublingual delivery systems include, but are not limited to, dissolvable tabs under and on the tongue, liquid drops, and beverages. Edible films, hydrophilic polymers, oral dissolvable films or oral dissolvable strips can be used. Other useful delivery systems comprise oral or nasal sprays or inhalers, and the like. Beverage embodiments are contemplated with flavor enhancements and/or various flavors added, as appropriate.

The nutritional compositions are preferably in unit dosage forms. In such form, the preparation is subdivided into unit doses containing appropriate quantities of the active component(s). The unit dosage form can be a packaged preparation, the package containing discrete quantities of preparation, such as packaged gum pieces, tablets, capsules, and powders in vials or ampoules. Also, the unit dosage form can be a gum piece, capsule, tablet, cachet, or lozenge itself, or it can be the appropriate number of any of these in packaged form.

Gum formulations are preferred. In one embodiment, the nutritional composition may be in the form of a gum product.

In accordance with other embodiments, carbonated beverage versions that use the same herbal/nutraceutical formulations as their gum counterparts can be used. Although, not offering the same contact time in the mouth as a gum delivery system, the light carbonation is believed to push the actives into the blood vessels of the mouth more quickly, thus providing a virtually identical sublingual effect—but in a form acceptable to those who do not wish to chew gum. Carbonated beverage embodiments are contemplated with flavor enhancements and/or various flavors added, as appropriate.

For oral administration, the bioactive components may be combined with one or more solid inactive ingredients for the preparation of gum pieces, tablets, capsules, pills, powders, granules or other suitable dosage forms. For example, the active agent may be combined with at least one excipient such as fillers, binders, humectants, disintegrating agents, solution retarders, absorption accelerators, wetting agents, absorbents, or lubricating agents. Other useful excipients include magnesium stearate, calcium stearate, mannitol, xylitol, sweeteners, starch, carboxymethylcellulose, microcrystalline cellulose, silica, gelatin, silicon dioxide, and the like.

The nutraceutical compositions of the present invention may be administered in combination with a nutraceutically acceptable carrier. The active ingredients in such formulations may comprise from 1% by weight to 99% by weight, or alternatively, 0.1% by weight to 99.9% by weight. "Nutraceutically acceptable carrier" means any carrier, diluent or excipient that is compatible with the other ingredients of the formulation and not deleterious to the user.

In accordance with one embodiment, a method for reduction of stress is provided, comprising administering to an individual in need thereof a nutraceutically effective amount of a combination of Ashwagandha herb and L-theanine. The combination of Ashwagandha herb and L-theanine is a nutritional composition or functional food in combination with a nutraceutically acceptable carrier.

In accordance with another embodiment, a method for enhancing energy and/or increasing mental clarity is provided, comprising administering to an individual in need thereof a nutraceutically effective amount of a combination of Ashwagandha herb and L-theanine. The combination of Ashwagandha herb and L-theanine is a nutritional composition or functional food in combination with a nutraceutically acceptable carrier.

Solid nutritional compositions for oral administration in connection with a method for promoting reduction of stress and enhancing energy may optionally contain, in addition to the above enumerated nutritional composition ingredients or compounds: carrier materials such as corn starch, gelatin, acacia, microcrystalline cellulose, kaolin, dicalcium phosphate, calcium carbonate, sodium chloride, alginic acid, and the like; disintegrators including, microcrystalline cellulose, alginic acid, and the like; binders including acacia, methylcellulose, sodium carboxymethylcellulose, polyvinylpyrrolidone, hydroxypropyl methylcellulose, ethyl cellulose, and the like; and lubricants or flow agents such as magnesium stearate, calcium stearate, stearic acid, silicone fluid, talc, waxes, oils, colloidal silica, and the like. The usefulness of such excipients is well known in the art.

Liquid nutritional compositions for oral administration in connection with a method for promoting reduction of stress and enhancing energy can be prepared in water or other aqueous vehicles. In addition to the above enumerated ingredients or compounds, liquid nutritional compositions can include suspending agents such as, for example, methylcellulose, alginates, tragacanth, pectin, kelgin, carrageenan, acacia, polyvinylpyrrolidone, polyvinyl alcohol, and the like. The liquid nutritional compositions can be in the form of a solution, emulsion, syrup, gel, or elixir including or containing, together with the above enumerated ingredients or compounds, wetting agents, sweeteners, and coloring and flavoring agents. Various liquid and powder nutritional compositions can be prepared by conventional methods.

In one embodiment, the nutritional composition will be in the form of a gum. A gum formula allows for release of the active components into saliva, which maximizes their contact time with the blood vessels inside the mouth. The actual process used in manufacturing the gum is designed to optimize this effect even further.

In accordance with one embodiment, a method of making a nutritional gum composition is provided. A cold compressed gum format is used which allows for the greatest consistency of functional ingredients in each piece of gum. Unlike traditional, extruded gum, cold compression technology uses no heat or moisture during manufacturing. This assures that substantially no actives are lost in manufacturing and consequently, about 100% release of actives during consumption. This manufacturing technique enables a work process including very fragile active ingredients such as probiotics that would not survive a conventional extruded gum manufacturing process.

Controlled temperature and humidity operations are employed, with generally no high temperature exposures, in the gum compression and sugar free coating processes so that all of the active ingredients maintain their efficacy and potency. This allows for very precise dosage and accurate and consistent delivery of functional ingredients. In production, the powdered active and inactive ingredients are blended, and compressed using a pharmaceutical grade, Fette tablet press (Fette America, Rockaway, N.J.). Optionally, the gumbase can be liquefied at a low temperature thus purifying the gum base. The liquified base can be poured into a mixer that blends the ingredients. Sweeteners, flavors, and bioactives (optionally, microencapsulated so as not to affect the flavor) are added and then slowly mixed in. The gum mixture is then sent to a press, which stamps out the circular pieces of gum. The gum pieces are then moved to a temperature-controlled environment to cool. This ensures the finished product will have the right consistency and stay fresh on store shelves.

In an embodiment, after a controlled, low-temperature heat treatment (referred to as "tempering"), the gum pieces are then fed into a spray drier that forms a crunchy coating around the center. It tumbles the pieces while a prepared syrup mixture, made of filtered water, sweeteners, and coloring, is sprayed onto the gum piece(s). This combination of tumbling and spraying forms a candy shell around the soft centers. The dried shell coating generally covers the gum-based centers of the gum pieces as an exterior layer, and alternatively, substantially completely covers the gum-based centers of the gum pieces. In an embodiment, the coating completely encapsulates the gum-based centers of the gum pieces.

In another embodiment, the gum pieces are loaded into conventional panning equipment. One or more layers of polyol syrup are applied using a sprayer or ladle. The rotational motion of the pan facilitates the spreading and subsequent drying of the syrup, forming a crunchy shell that covers the gum pieces. The dried shell coating generally covers the gum-based centers of the gum pieces as an exterior layer, and alternatively, substantially completely covers the gum-based centers of the gum pieces. In an embodiment, the coating completely encapsulates the gum-based centers of the gum pieces.

The nutritional composition and methods described above may be further understood in connection with the following Examples.

Example 1A

Gum Formulation

A representative serving of nutritional gum may include or consist of the following ingredients of Table 1:

TABLE 1

| Ingredient | Range (mg) |
|---|---|
| Gum base | 400-600 |
| Sorbitol | 380-440 |
| Xylitol | 250-310 |
| Isomalt | 215-235 |
| Maltitol | 190-230 |
| L-Theanine | 50-125 |
| Ashwagandha extract | 80-150 |
| Magnesium stearate | 50-55 |
| 90% Stevia extract | 8.0-12.0 |
| Silicon dioxide | 4.0-5.0 |
| Titanium dioxide | 2.0-4.0 |
| Carnauba wax | 1.5-2.5 |
| Confectioner's glaze | 1.5-2.5 |
| modified food starch | 2.5-3.5 |
| natural and artificial flavors | 90-110 |
| Gum Piece Total | 1724.5-2284.5 |

Example 1B

Gum Preparation

In accordance with one embodiment, a serving of a nutritional gum composition is prepared. The following ingredients are blended: Ashwagandha Root Extract powder (80 mg to 150 mg), L-theanine (50 mg to 125 mg), gumbase, sorbitol, isomalt, xylitol, maltitol, magnesium stearate, natural and artificial flavors, modified food starch, stevia extract, carnauba wax, silicon dioxide, titanium dioxide, and confection glaze, as follows (on a scale appropriate to produce multiple servings). A powdered gumbase is manufactured by blending different gumbase compositions with the other ingredients through a series of mixing, drying and milling steps at temperatures ranging between 60° F. and 210° F. (about 15° C. to about 100° C.). The resulting gum powder is sent to a tablet press, which stamps out the circular pieces of gum. The gum pieces are then loaded into conventional panning equipment. One or more layers of polyol syrup are applied using a sprayer or ladle. In this embodiment, the polyol syrup can include several sugar alcohols indicated above including maltitol, xylitol, and isomalt. The rotational motion of the pan facilitates the spreading and subsequent drying of the syrup, forming a crunchy shell that covers the gum pieces. The gum pieces are then held for a minimum of 12 hours before packaging. Each gum piece comprises one serving.

Optionally, the syrup is made using mainly sugar alcohols and other ingredients for taste and/or color. This would include panning using maltitol, xylitol, isomalt or any other "sugar-free" (specifically, free of sucrose) ingredients. Optionally, other customized flavoring and/or coloring systems can be used.

Example 1C

In one embodiment, the gum ingredients are blended as in Example 1B, using Ashwagandha Root Extract powder (70 mg to about 110 mg) and L-theanine (80 mg to about 120 mg).

Example 2

Stress Reduction Method

In accordance with an embodiment, it is expected that an individual human subject using the nutritional gum composition of Example 1 by chewing at least one serving, or otherwise consuming in a sublingual fashion, will experience a sensation of relaxation and yet alertness without accompanying drowsiness or sedation. In a variation, it is expected that an individual will benefit from an anxiolytic effect, by chewing at least one serving of the nutritional gum composition of Example 1. In a further variation, it is expected that an individual will experience an enhancement of energy, mental alertness, clarity or acuity and improvement of concentration, by chewing at least one serving of the nutritional gum composition of Example 1.

Example 2A

Stress Reduction Method

In accordance with the method of Example 2, a serving containing 100 mg L-theanine and 80 mg Ashwagandha Root Extract powder is chewed by a human individual. Optionally, within about 10 minutes to 1 hour, a second serving is chewed by the individual. It is expected that the individual will experience a sensation of relaxation and yet alertness without accompanying drowsiness or sedation after several minutes, for example, after about 10 minutes. In a variation, it is expected that an individual will benefit from an anxiolytic effect, by chewing at least one serving of the nutritional gum composition after several minutes. In a further variation, it is expected that an individual will experience an enhancement of energy, mental alertness, clarity or acuity and improvement of concentration, by chewing at least one serving of the nutritional gum composition after several minutes.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

I claim:

1. A nutritional gum composition comprising Ashwagandha herb and L-theanine in combination with a nutraceutically acceptable carrier, wherein Ashwagandha herb is provided in a range from about 140 mg to about 200 mg per dose, and L-theanine is provided in a range from about 160 mg to about 240 mg per dose.

2. The nutritional gum of claim 1, wherein Ashwagandha herb is and L-theanine are provided in one or more servings.

3. A sublingual dietary supplement composition comprising Ashwagandha herb and L-theanine in combination with a nutraceutically acceptable carrier wherein the composition is a gum piece, wherein Ashwagandha herb is provided in a range from about 140 mg to about 200 mg per dose, and L-theanine is provided in a range from about 160 mg to about 240 mg per dose.

4. The sublingual dietary supplement composition of claim 3, wherein Ashwagandha herb is provided in a range from about 150 mg to about 180 mg per dose, and L-theanine is provided in a range from about 180 mg to about 220 mg per dose.

* * * * *

UNITED STATES PATENT AND TRADEMARK OFFICE
CERTIFICATE OF CORRECTION

| | | |
|---|---|---|
| PATENT NO. | : 8,636,985 B2 | Page 1 of 1 |
| APPLICATION NO. | : 13/296034 | |
| DATED | : January 28, 2014 | |
| INVENTOR(S) | : Jon Barron | |

It is certified that error appears in the above-identified patent and that said Letters Patent is hereby corrected as shown below:

IN THE CLAIMS:

In Claim 2, Column 12, line 18, delete the word "is".

Signed and Sealed this
Seventeenth Day of February, 2015

Michelle K. Lee
*Deputy Director of the United States Patent and Trademark Office*